(12) United States Patent
Sovak et al.

(10) Patent No.: US 7,250,153 B2
(45) Date of Patent: Jul. 31, 2007

(54) CONTRAST MEDIA FORMULATIONS HAVING IMPROVED BIOLOGICAL TOLERANCE

(75) Inventors: Milos Sovak, Rancho Santa Fe, CA (US); Allen L. Seligson, Ramona, CA (US); Ronald C. Terry, San Diego, CA (US)

(73) Assignee: Biophysica Research, Inc., La Jolla, CA (US)

(*) Notice: Subject to any disclaimer, the term of this patent is extended or adjusted under 35 U.S.C. 154(b) by 624 days.

(21) Appl. No.: 10/701,586

(22) Filed: Nov. 5, 2003

(65) Prior Publication Data

US 2005/0025711 A1 Feb. 3, 2005

Related U.S. Application Data

(60) Provisional application No. 60/432,879, filed on Dec. 12, 2002.

(51) Int. Cl.
*A61K 49/04* (2006.01)

(52) U.S. Cl. .................................................. 424/9.452
(58) Field of Classification Search ............... 424/9.45, 424/9.451, 9.453, 9.4, 9.452; 564/153
See application file for complete search history.

(56) References Cited

U.S. PATENT DOCUMENTS 4,396,597 A    8/1983    Rakli et al.
5,698,739 A * 12/1997    Sovak ..................... 564/153

FOREIGN PATENT DOCUMENTS

DE    196 48 650 A1    7/1997

\* cited by examiner

*Primary Examiner*—Michael G. Hartley
*Assistant Examiner*—Leah Schlientz
(74) *Attorney, Agent, or Firm*—Peters Verny, LLP

(57) ABSTRACT

This invention comprises new formulations of radiographic contrast media including dimeric non-ionic media, with an organic amine and a carboxylic acid. Formulations of this invention increase the biological tolerance of such media, thereby increasing their safety.

7 Claims, No Drawings

CONTRAST MEDIA FORMULATIONS HAVING IMPROVED BIOLOGICAL TOLERANCE

CLAIM OF PRIORITY

This application claims priority to U.S. Provisional Patent Application No. 60/432,879, filed on Dec. 12, 2002, which is hereby incorporated by reference in its entirety.

FIELD OF THE INVENTION

This invention deals with radiographic contrast media (RCM). Specifically, this invention relates to dimeric non-ionic contrast media and especially a dimeric primary carboxamide iosimenol and methods for improving biological tolerance by formulating such media in buffers containing organic amines and carboxylic acids.

BACKGROUND

Radiographic contrast media are indispensable tools of medical imaging of the body cavities and organ systems. They are typically given as highly concentrated solutions and in large volumes and thus must possess a high degree of biological tolerance. RCM must be nontoxic. Because of the large volumes used, RCM can feasibly be sterilized only by standard autoclaving, i.e. 20 minutes at 121° C. While chemo-physically stable at physiological pH and ambient temperatures, at high temperatures all RCM, including the dimeric non-ionic RCM such as iosimenol (N,N'-Bis[3-carbamoyl-5-(2,3-dihydroxypropyl-carbamoyl)-2,4,6-tri-iodophenyl]-N,N'-bis(2,3-dihydroxypropyl)-malonamide), which contain a hydroxy group in the β-position of the N-hydroxyalkyl group, unless at acidic pH, can partially decompose as indicated by the release of free iodide. The emergence of high levels of free iodide compromises the thyroid functions and would therefore be undesirable. Although a number of conventional buffers such as citrates and other carboxylates, lactates, carbamates, acetate/acetic acid, phosphates, glycine and the like have a broad use in the preparation of many parenteral solutions, they do not prevent destabilization of RCM exposed to high temperature during autoclaving, especially at pH ranges over 7.0.

Intravenous pharmaceuticals are conventionally buffered to a physiologically acceptable pH range of 5.5-7.5. Aqueous solutions of all RCM in clinical use are usually buffered with organic amines such as TRIS and a mineral acid such as HCl, with a small amount of a chelating agent such as Ca/Na EDTA added. When organic carboxylic acids are used alone, they are known to destabilize RCM at higher temperatures, thereby resulting in their partial destruction. According to the prior art, addition of an organic amine with carboxylic acid to the RCM in a neutralizing, equivalent ratio, improves the stability of RCM during autoclaving and storage. However, this approach is not applicable to every RCM, and specifically was shown not to work for iosimenol. If formulated according to the prior art methods with a carboxylic acid neutralized by an amine, iosimenol under autoclaving unexpectedly became less stable than when formulated in TRIS with a carboxylic acid in ratios where TRIS prevailed, or in a commonly used TRIS/HCl buffer.

SUMMARY

The present invention is based on the unexpected finding that dimeric non-ionic contrast media, such as iosimenol, in newly discovered formulations containing a carboxylic acid, such as citric acid, and an amine in excess tolerated autoclave sterilization, while the systemic biological tolerance of such formulations was unexpectedly and significantly increased compared to standard formulations. In certain embodiments, the ratio of the amine and acid is selected to provide greater biological tolerance.

DETAILED DESCRIPTION

This invention pertains to novel application of certain unique properties of dimeric non-ionic contrast media (RCM), such as iosimenol, which while based on primary carboxamides, represents a new class of RCM. Iosimenol in aqueous solutions, like other RCM, is used in large volumes for injections into the cardiovascular and other organ systems and body cavities. Since RCM are diagnostic devices and drugs only by default, they should be as biologically inactive as possible, a goal to which a search for improved formulations should contribute. Embodiments of this invention improve upon the prior art formulations in that they provide greater biological tolerance when given in the typically large amounts needed for radiographic uses. Although there has been extensive work carried out to improve RCM, prior art methods of formulation may not have been optimized. In particular, as described above, formulating dimers such as iosimenol with buffers containing amines and an inorganic acid, as in prior art RCM, has not provided the optimal biological tolerance.

In general, the decomposition of RCM can be substantially reduced by buffer systems that lower the pH during autoclaving. Such temperature dependent buffers comprise the prevalent formulation of the clinically used RCM, and make use of certain amines, including tromethanol (TRIS), typically added in concentrations varying from 10-20 mM (Rakli et al., U.S. Pat. No. 4,396,597, incorporated fully by reference). Unlike inorganic buffers, TRIS/HCl transiently decreases pH during autoclaving and the solution's pH returns to the starting value once the ambient temperature has been reached. Significantly, however, the inventors of the above patent stated, "in formulating the solutions for autoclaving with TRIS, it is generally preferred to ensure that no anions such as carboxylates be present."

German Patent DE19648650C2 with the priority of 290196 by Sachse et al. (incorporated herein fully by reference) stated that they improved the stability of a number of parenteral preparations including RCM, by addition of at least one organic acid, including a carboxylic acid, to TRIS or N-methyl glucamine. To demonstrate the advantage of such combined buffers for the purpose of increasing the stability, the inventors of the above patent used a known nonionic monomer RCM, iopromide. They demonstrated by examples that with pH adjusted from 6.5 to 7.5, following standard autoclaving, iopromide formulated in TRIS and a variety of carboxylic acids, always in equivalent molar ratio, has released substantially less iodide (indicative of decomposition) than when formulated with TRIS/HCl buffer. Having assumed that this finding would be applicable to all RCM and any ratio of an organic amine and an organic acid, the authors have published a corresponding general claim which does not mention the equivalent molar ratio but only a mix of amine and an organic acid, for the previously stated purpose of increasing the stability of RCM.

We found that improved stability as found for prior art monomeric RCMs does not apply to dimeric non-ionic contrast media, including iosimenol. At a pH in the range of about 6.5 to 7.5 in a buffer containing 20 mM TRIS and 5 mM citric acid, iosimenol is always somewhat less or equally stable than when autoclaved with the TRIS/HCl buffer or with TRIS/citrate in molar equivalent ratio (Table 1). This means that the stability of dimeric non-ionic contrast media such as iosimenol is not improved by combining TRIS with citric acid in molar equivalent concentrations and that the molecular structure of iosimenol, which differs conceptually from other RCM, is not subject to the stability improvement of monomeric non-ionic RCM in TRIS/citrate buffers as disclosed by Sachse et al.

Thus, in certain embodiments of this invention, the molar ratio of TRIS to citrate is above about 3:1. In alternative embodiments, the ratios are above about 3 to about 10, above 3 to about 9, above 3 to about 8, above 3 to about 7, above 3 to about 6, above 3 to about 5, and above 3 to about 4. Thus, if the TRIS concentration is 10 mM, the citrate concentration should be below about 3.3 mM, if the TRIS concentration is 20 mM, the citrate concentration should be below about 6.6 mM, and if the TRIS concentration is 30 mM, the citrate concentration should be below about 10 mM. In other embodiments which comprise organic amines and/or carboxylic acids having different numbers of equivalents than TRIS (3 equivalents per mole) or citric acid (1 equivalent per mole), the ratio of equivalents of organic amine to carboxylic acid is desirably greater than 1:1 (i.e., the amine is in an excess of equivalents compared to the carboxylic acid).

Because dimeric non-ionic contrast media such as iosimenol have twice the number of iodine atoms per mole of RCM, the total molecular concentration of RCM in a solution is less than that for a monomeric RCM having the same iodine concentration. Thus, for a given total iodine concentration, the osmolality of the dimeric RCM is always less than that of the monomeric RCM. To ensure that the solution that is used clinically has a physiological osmotic pressure, such RCM solution can comprise other physiologically acceptable materials, such as increased concentrations of TRIS or the buffers of this invention or inorganic or organic physiologically acceptable salts.

To manufacture formulations as described above, a dimeric RCM is combined with a buffer comprising a carboxylic acid and an amine. Thus, in certain embodiments of this invention, the molar ratio of TRIS to citrate is above about 3:1. In alternative embodiments, the ratios are above about 3 to about 10, above 3 to about 9, above 3 to about 8, above 3 to about 7, above 3 to about 6, above 3 to about 5, and above 3 to about 4. Thus, if the TRIS concentration is 10 mM, the citrate concentration should be below about 3.3 mM, if the TRIS concentration is 20 mM, the citrate concentration should be below about 6.6 mM, and if the TRIS concentration is 30 mM, the citrate concentration should be below about 10 mM. In other embodiments which comprise organic amines and/or carboxylic acids having different numbers of equivalents than TRIS (3 equivalents per mole) or citric acid (1 equivalent per mole), the ratio of equivalents of organic amine to carboxylic acid is desirably greater than 1:1 (i.e., the amine is in an excess of equivalents compared to the carboxylic acid). After formulation, the mixture is sterilized, such as by autoclaving and then is packaged.

To use the formulations of this invention, a subject is prepared for radioscopic examination, and a desired amount of dimeric RCM in a buffer comprising a carboxylic acid and an amine. Formulations can be injected intravenously, or into any desired body cavity. When the formulation of RCM has been distributed sufficiently, radioscopic examination of the organ or tissue is then carried out using conventional methods (e.g., such as x-ray).

It can be appreciated that in addition to iosimenol, other dimeric RCM can advantageously be formulated using the buffer systems of this invention. Other such dimeric RCM include iodixanol, iotrolan and the like.

EXAMPLES

The following Examples illustrate methods and formulations according to the invention and are not intended to limit the scope of the invention. Other specific embodiments can be developed and used without departing from the scope of this invention and without undue experimentation. All such embodiments are considered part of this invention.

Example 1

Stability of Iosimenol to Autoclave Sterilization in the Presence of TRIS and Citrate Samples of Iosimenol were formulated in 20 mM TRIS+5 mM citric acid, TRIS/HCl and 10 mM TRIS+3.3 mM citrate. Samples were then autoclaved for 20 minutes at 121° C. and the amounts of free iodine measured. Results are presented in Tables 1a-1c.

Tables 1a-1c

Stability of Iosimenol after 20 Minutes at 121° C.

TABLE 1a

Buffer: 20 mM TRIS + 5 mM citric acid

| | $I^-$ μg/ml | |
|---|---|---|
| | before | after |
| | 3.59 | 16.53 |
| | 4.44 | 18.87 |
| | 4.52 | 18.13 |
| | 4.08 | 15.80 |
| | 3.94 | 15.96 |
| | 3.42 | 16.11 |
| Avg. | 4.00 | 16.90 |
| $\Delta I^-$ | | +12.90 |

TABLE 1b

Buffer: 20 mM TRIS/HCl

| $I^-$ μg/ml | |
|---|---|
| before | after |
| 4.29 | 14.07 |
| 4.44 | 14.19 |
| 4.27 | 14.39 |
| 4.33 | 14.22 |
| +9.89 | |

TABLE 1c

Buffer: 10 mM TRIS + 3.3 mM citrate

| | $I^-$ μg/ml | |
|---|---|---|
| | before | after |
| | 3.99 | 22.34 |
| | 4.17 | 21.51 |
| | 3.83 | 21.66 |
| Avg. | 4.00 | 21.84 |
| $\Delta I^-$ | | +17.84 |

In a separate study, iosimenol formulated in TRIS/citric acid in a non-equivalent ratio, after autoclaving (121° C. for 20 min) had lower stability than in TRIS/HCl buffer, with the pre-autoclaving pH at 7.00, and Ca/Na EDTA 0.1 mg/ml, and concentration of RCM at 340-355 mg I/ml, the following was observed (Table 2).

TABLE 2

Stability of Iosimenol in TRIS/HCl and equivalent TRIS/Citric Acid

| Buffers | pH after autoclaving | $\Delta I^-$ ($\mu$g/ml) |
|---|---|---|
| 10 mM TRIS/HCl | 6.49 | +8.7 |
| 20 mM TRIS/HCl | 7.00 | +7 |
| 10 mM TRIS + 3 mM citric acid | 6.90 | +24.2 |

Thus although we have shown that the stability of iosimenol solutions could not be improved by a buffer consisting of equivalent ratio of TRIS and citric acid compared to TRIS/HCl, we found that the formulation 20 mM TRIS with 5 mM citric acid unexpectedly substantially improved iosimenol's systemic tolerance (see Example 2 below).

Example 2

In vivo Tolerance of Iosimenol

To examine the effects of the TRIS/citrate buffer system of this invention on the biological tolerance, using standard methods, we assessed intravenous murine and rat $LD_{50}$ of iosimenol formulated either in TRIS/HCl or in the novel TRIS/citric acid buffers, and compared the results with those published for the clinically employed nonionic dimer iodixanol (formulated in TRIS/HCl buffer; Heglund IF et al., Acta Radiol. Suppl. 1995:399:69-82). Murine and rat $LD_{50}$ were obtained by 1 ml/min injection of 340 mg I/ml; data at 7 days and based on the 50% survival of the animals was expressed as g I/kg bw (Table 3). Unexpectedly, we found statistically significantly higher $LD_{50}$ for iosimenol formulated in 20 mM TRIS with 5 mM citrate than in 20 mM TRIS/HCl.

TABLE 3

Effects of Buffer on Systemic (Intravenous) Tolerance of Iosimenol* in rats and mice

| | Control: Iodixanol (TRIS/HCl) | Iosimenol (20 mM TRIS + 5 mM citric acid) | Iosimenol (20 mM TRIS/HCl) |
|---|---|---|---|
| $LD_{50}$ mice | 21.0 | 26.0 | 22.0 |
| $LD_{50}$ rats | 21.0 | 23.5 | 20.0 |

While the mechanisms of this finding have not been identified, the novel TRIS/citrate formulation of this invention improved the systemic tolerance of iosimenol significantly and is expected to do so in the clinical applications.

Both TRIS and citric acid are approved inert substances and authorized to be used as excipients, for buffering purposes, in intravenous solutions under the definition of the FDA Guide of January 1996 21CFR210.3 (B)8,7. It has been demonstrated that addition of 6 mM citrate to non-ionic RCM did not induce cardiovascular changes of clinical significance, as they were smaller than those induced by the ionic dimer ioxaglate (Morris and Rubinstein, 1991).

Because the osmolality of typical diagnostic solutions of iosimenol, if unadjusted, would be less than the physiological value of 310 mOsm, a more concentrated buffer can be used, for example 50 mM, more preferably 10 to 25 mM of TRIS, and an acceptable ionic substance such as NaCl or an amino acid salt can be added to adjust the osmolality of the RCM solution.

Processes for formulation of a physiologically and pharmaceutically acceptable solution of dimeric non-ionic contrast media including iosimenol comprises its formulation with TRIS/citrate at a ratio of at least 3:1 then autoclaving the resulting solution at 121° C. for 20 min. It can be appreciated that other organic amines can be used, as well as other carboxylic acids, instead of TRIS and citrate, so long as the ratio of equivalents of the organic amine to the carboxylic acid is greater than 1:1.

The novel buffer formulations improved the systemic tolerance of iosimenol in the in vivo studies described herein, and the results are directly applicable to clinical use in humans and other species.

Example 3

Measurement of Iodide Content of RCM Preparations Methods

1. Determination of Iodide by HPLC

A 5 micron $C_{18}$ column 25 cm×4.6 mm ID was eluted with 30% acetonitrile/70% 0.05 M $KH_2PO_4$ containing 7 ml/L of 40% tetrabutyl ammonium hydroxide. 20 µl of a 10 µg $I^-$/ml was the standard. 20 µl of a test sample of iosimenol was injected and UV absorbance measured at 230 nm, 0.2 AU. Under these conditions, the iodide standard eluted after 5.6 minutes and gave an area of "X" counts. An experimental sample of an autoclaved solution of contrast medium was injected, and an iodide peak at 5.6 minutes resulted in an area count of "Y." The experimental sample's iodide level was Y/X×10 µg/ml=Z µg $I^-$/ml.

2. Determination of Iodide by Spectrophotometry

Iodide was alternately determined by extraction and spectrophotometry according to USP24/NF19, p 911 (1995). In general, the solution containing iodide is oxidized in the presence of acid, with sodium nitrite and then extracted into toluene which is then read at a wavelength of 500 nm. Comparison of standard samples with experimental samples yields the amount of iodide present in the sample.

CONCLUSIONS

Dimeric non-ionic contrast media such as iosimenol in buffers comprising an organic amine and a carboxylic acid such as citric acid, wherein the molar ratio of amine to acid is at least 3:1 produces a preparation of primary carboxamide dimeric RCM having improved biological tolerance. The disclosed formulations can produce a significantly greater tolerated dose of RCM. This increase in tolerated dose is completely unexpected and should provide for increased safety of the title compounds in medical imaging.

INDUSTRIAL APPLICABILITY

This invention finds use in the health care industry, in which radiopaque contrast media are used to visualize interior spaces within a body, such as blood vessels, body cavities, spaces in body organs, or cavities in the nervous system. The formulations also find use in the pharmaceutical industry in the manufacture of radiopaque contrast media and kits for sale to physicians, hospitals, diagnostic centers and other health-care providers.

We claim:

1. A formulation having improved biological tolerance and a physiologically acceptable pH and osmolality comprising a sterile aqueous solution of iosimenol (1-N,N'-Bis[3-carbamoyl-5-(2,3-dihydroxypropyl-carbamoyl)-2,4,6-triiodophenyl]-N,N'-bis(2,3-dihydroxypropyl)-malonamide); and a buffer comprising: TRIS and citrate, wherein the molar ratio of TRIS to citrate is in the range of greater than 3:1 to about 10:1 and said TRIS is at a concentration in the range of about 5 to 40 mM.

2. The formulation of claim 1, further comprising a chelating agent.

3. The formulation of claim 2, wherein said chelating agent is selected from the group consisting of Ca/Na EDTA and EDTA.

4. A kit for use in radiographic examinations, comprising: a vial containing a solution comprising: a dimeric non-ionic contrast medium; and a buffer comprising: an organic amine; and a carboxylic acid formulation having improved biological tolerance and a physiologically acceptable pH and osmolality comprising a sterile aqueous solution of iosimenol (1-N,N'-Bis[3-carbamoyl-5-(2,3-dihydroxypropyl-carbamoyl)-2,4,6- triiodophenyl]-N,N'-bis(2,3-dihydroxypropyl)-malonamide); and a buffer comprising: TRIS and citrate, wherein the molar ratio of TRIS to citrate is in the range of greater than 3:1 to about 10:1 and said TRIS is at a concentration in the range of about 5 to 40 mM; and instructions for use.

5. A method for radiographic examination of a subject, comprising:
   a. delivering a contrast medium to an area to be visualized in said subjects body or by intravenous injection; and
   b. visualizing said area, wherein said contrast medium is a formulation, having improved biological tolerance and a physiologically acceptable pH and osmolality, comprising a sterile aqueous solution of iosimenol (1-N,N'-Bis[3-carbamoyl-5-(2,3 -dihydroxypropyl-carbamoyl)-2,4,6- triiodophenyl]-N,N'-bis(2,3-dihydroxypropyl)-malonamide); and a buffer comprising: TRIS, and citrate, wherein the molar ratio of TRIS to citrate is in the range of greater than 3:1 to about 10:1 and said TRIS is at a concentration in the range of about 5 to 40 mM.

6. A formulation according to claim 1 sterilized by autoclaving.

7. A formulation according to claim 6, wherein said TRIS is present in an amount of 20 mM and said citrate is present in an amount of 5 mM.

* * * * *